(12) United States Patent
Murso et al.

(10) Patent No.: US 11,813,486 B2
(45) Date of Patent: Nov. 14, 2023

(54) CARTRIDGE AND BREATHING APPARATUS CONTAINING THE SAME

(71) Applicant: MSA Europe GmbH, Jona (CH)

(72) Inventors: Harry Murso, Berlin (DE); Juergen Unger, Ahrensfelde (DE)

(73) Assignee: MSA Europe GmbH, Jona (CH)

( * ) Notice: Subject to any disclaimer, the term of this patent is extended or adjusted under 35 U.S.C. 154(b) by 1283 days.

(21) Appl. No.: 16/332,043

(22) PCT Filed: Sep. 12, 2017

(86) PCT No.: PCT/EP2017/072851
§ 371 (c)(1),
(2) Date: Mar. 11, 2019

(87) PCT Pub. No.: WO2018/046751
PCT Pub. Date: Mar. 15, 2018

(65) Prior Publication Data
US 2019/0209875 A1   Jul. 11, 2019

(30) Foreign Application Priority Data

Sep. 12, 2016   (DE) ...................... 10 2016 217 325.1

(51) Int. Cl.
*A62B 19/00* (2006.01)
*A62B 7/00* (2006.01)
(Continued)

(52) U.S. Cl.
CPC ................ *A62B 19/00* (2013.01); *A62B 7/08* (2013.01); *C01B 13/0203* (2013.01);
(Continued)

(58) Field of Classification Search
CPC .. A62B 19/00; A62B 7/00; A62B 7/08; A62B 19/02; A61M 16/22; H01M 2300/0071; C01B 13/0203; B01D 53/62
See application file for complete search history.

(56) References Cited

U.S. PATENT DOCUMENTS

| 4,265,238 A | 5/1981 | Swiatosz et al. |
| 4,717,549 A * | 1/1988 | Malafosse .............. A62B 21/00 |
| | | 128/202.28 |

(Continued)

FOREIGN PATENT DOCUMENTS

| CN | 101041424 A | 9/2007 |
| CN | 102376379 A | 3/2012 |

(Continued)

*Primary Examiner* — Samchuan C Yao
*Assistant Examiner* — Yurie Hong
(74) *Attorney, Agent, or Firm* — Jones Day

(57) ABSTRACT

A chemical cartridge or an oxygen generating breathing apparatus includes an outer canister and an inner canister with an interior space. At least one alkali hyperoxide or earth alkali hyperoxide that can act as an electrolyte in the presence of moisture and at least one first metallic material are provided in the interior space of the inner canister. At least one second metallic material is provided between the inner canister and the outer canister or is at least partially integrated into the outer canister wall. Between the inner canister including the first metallic material and the outer canister including the second metallic material an ion-permeable material is arranged such that the cartridge generates electrical power when in use by creating a potential between the first metallic material and the second metallic material when the at least one alkali hyperoxide or earth alkali hyperoxide is contacted by $CO_2$ and moisture.

16 Claims, 2 Drawing Sheets

(51) Int. Cl.
  *A61M 16/22* (2006.01)
  *A62B 7/08* (2006.01)
  *C01B 13/02* (2006.01)
  *H01M 8/1009* (2016.01)
  *H02N 11/00* (2006.01)
  *B01D 53/62* (2006.01)
  *A62B 19/02* (2006.01)

(52) U.S. Cl.
  CPC ........ *H01M 8/1009* (2013.01); *H02N 11/002* (2013.01); *A62B 19/02* (2013.01); *B01D 53/62* (2013.01); *B01D 2257/504* (2013.01); *H01M 2250/30* (2013.01); *H01M 2300/0071* (2013.01)

(56) References Cited

U.S. PATENT DOCUMENTS

| | | | | |
|---|---|---|---|---|
| 4,963,327 | A | * | 10/1990 | Russell ................ A62B 19/00 422/305 |
| 2008/0085498 | A1 | | 4/2008 | Wezurek et al. |
| 2008/0276934 | A1 | | 11/2008 | Kruger et al. |
| 2014/0000594 | A1 | | 1/2014 | Rittner et al. |

FOREIGN PATENT DOCUMENTS

| | | |
|---|---|---|
| DE | 102006044951 B3 | 9/2007 |
| DE | 102014002906 A1 | 9/2015 |
| EP | 1838394 B1 | 6/2010 |
| EP | 2163278 B1 | 1/2015 |
| GB | 2011792 A | 7/1979 |

\* cited by examiner

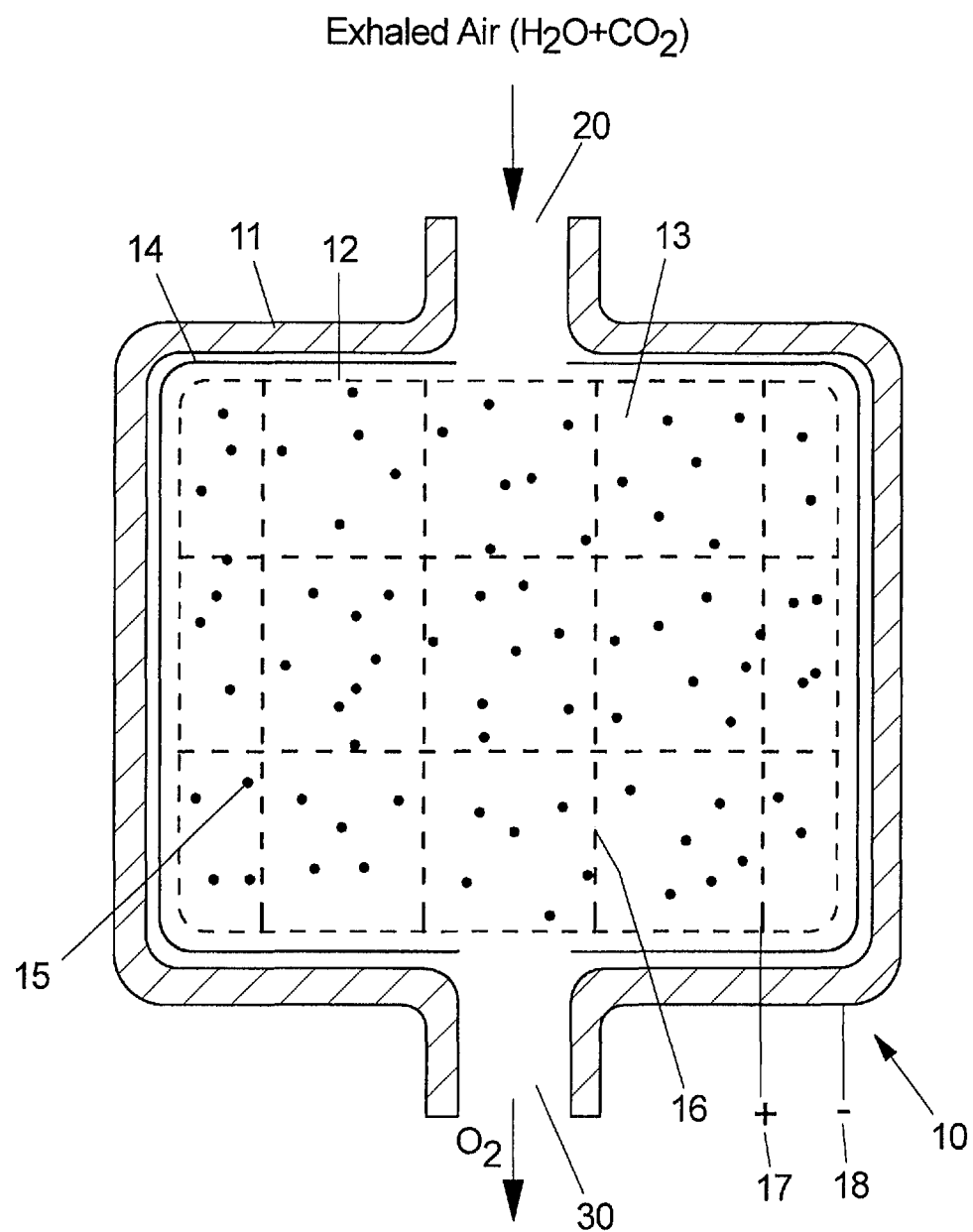

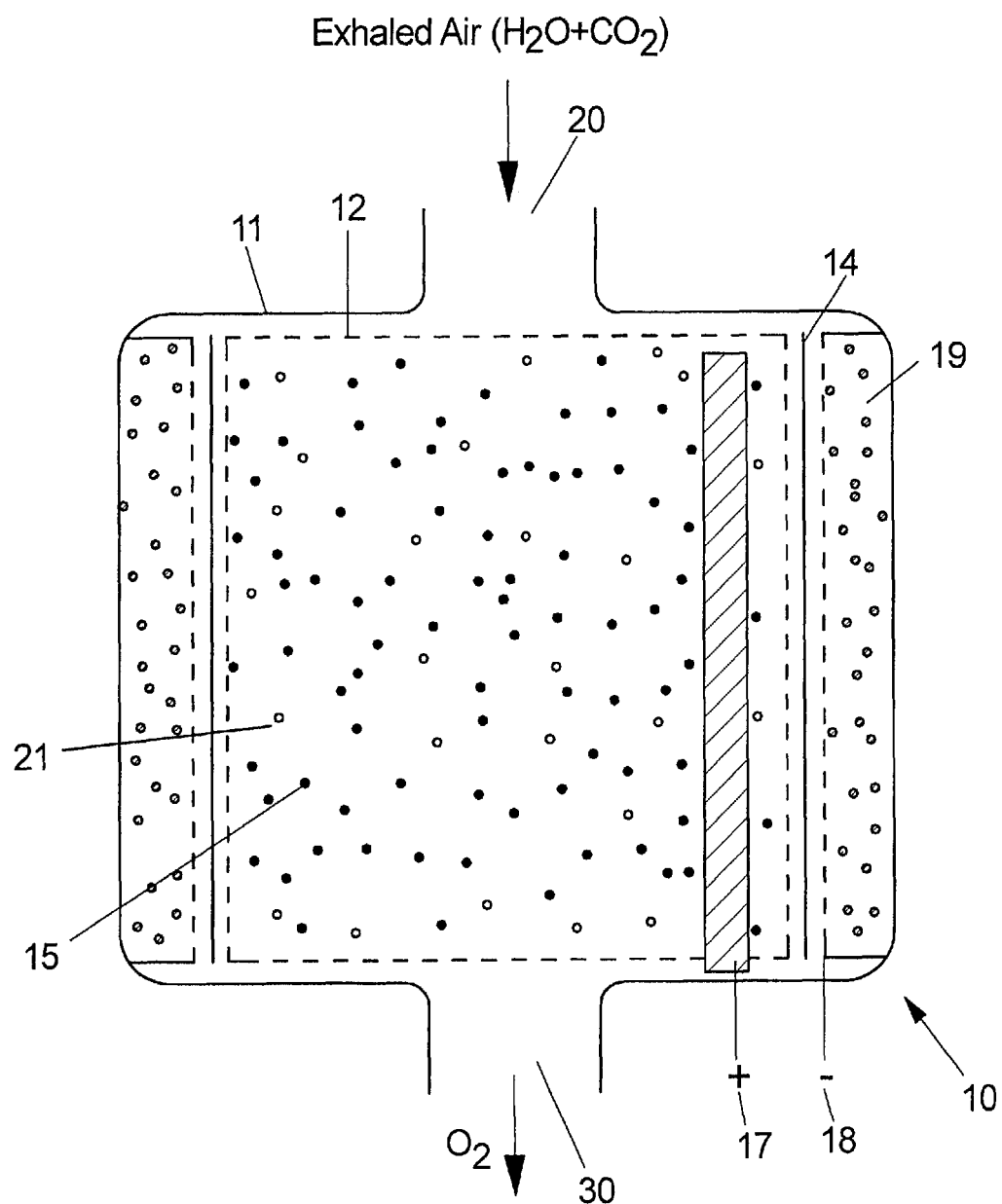

CARTRIDGE AND BREATHING APPARATUS CONTAINING THE SAME

CROSS-REFERENCE TO RELATED APPLICATIONS

This application is the United States national phase of International Application No. PCT/EP2017/072851 filed Sep. 12, 2017, and claims priority to German Patent Application No. 10 2016 217 325 filed Sep. 12, 2016, the disclosure of each of which is hereby incorporated by reference in its entirety.

BACKGROUND OF THE INVENTION

Field of the Invention

The present invention relates to a Closed Circuit Breathing Apparatus (CCBA) and, more particularly, to a chemical cartridge for an oxygen breathing apparatus.

Description of Related Art

A Closed Circuit Breathing Apparatus (CCBA) allows the user to work in dangerous areas for up to about 4 hours. The CCBA uses an oxygen source comprised of either a high pressure oxygen cylinder or chemically generated oxygen. In a breathing apparatus of the latter type, the exhaled air of the user is passed over a chemical located in a canister or a chemical cartridge, for example, potassium hyperoxide ($KO_2$) present in granular form. The moisture and carbon dioxide present in the exhaled air reacts with the potassium hyperoxide, and oxygen is generated in an exothermic reaction, according to the following equations:

$$4KO_2 + 2H_2O \rightarrow 4KOH + 3O_2 \quad (I)$$

$$4KO_2 + 4CO_2 + 2H_2O \rightarrow 4KHCO_3 + 3O_2 \quad (II)$$

The generated oxygen is subsequently passed from the chemical cartridge into a breathing bag and is then inhaled by the user. The exhaled $CO_2$ may be at least partially absorbed by the $KO_2$ (see above equation II) or may be absorbed by an additional $CO_2$ absorber, such as soda lime in case of high pressure oxygen.

For monitoring, warning, or support of important functionalities, all CCBA's need additional electrical power. In current applications the electrical power is provided by batteries or accumulators. However, the increasing need for electrical power (for example due to additional or more sophisticated monitoring equipment) requires more electrical capacity. Different approaches were suggested in the past for providing additional electrical power, such as using thermal effects, piezo-electrical effects for generating energy, or adding more batteries. All these suggestions require additional parts and add to the overall weight to be carried by the user.

Thus, there is a need in the field of breathing systems to limit or reduce the weight of batteries or accumulators to be carried by the user of a CCBA.

SUMMARY OF THE INVENTION

Generally, provided are an improved apparatus and method for generating oxygen in a breathing apparatus. Preferably, provided is a cartridge for a breathing apparatus that can generate electrical energy and reduce the weight of required batteries or accumulators and thereby reduce the total weight of the CCBA significantly.

According to a preferred and non-limiting embodiment, example, or aspect, provided is a chemical cartridge for a breathing apparatus, in particular for an oxygen generating breathing apparatus, comprising an outer canister and an inner canister with an interior space provided.

In a preferred and non-limiting embodiment, example, or aspect, the interior space of the inner canister can include at least one alkali hyperoxide or earth alkali hyperoxide that can act as an electrolyte in the presence of moisture and at least one first metallic material. At least one second metallic material can be provided between the inner canister and the outer canister or optionally can be at least partially integrated into the outer canister wall.

In a preferred and non-limiting embodiment, example, or aspect, an ion permeable material can be arranged between the first metallic material in the inner canister and the second metallic material.

According to a preferred and non-limiting embodiment, example, or aspect, provided is a chemical cartridge for a breathing apparatus with multiple functions. The chemical cartridge can be an electrochemical cell that can function to generate oxygen and absorb $CO_2$. The chemical cartridge can allow for the generation of electrical energy when moist exhaled air contacts the hyperoxide present in the cartridge. The reaction of the hyperoxide with water can create an alkaline electrolyte solution (see for example above equation I) that can be in contact with both metallic materials. The alkaline electrolyte can provide a circuit between the first and second metallic materials (with different standard potentials) whereupon electrical energy can be generated. The chemical cartridge can provide electrical energy on demand (i.e., only when the breathing apparatus and the cartridge are used) without loss of potential capacity during storage. Additional batteries for power may not be required thereby reducing the weight of the breathing apparatus while simultaneously improving performance.

In a preferred and non-limiting embodiment, example, or aspect, the at least one alkali hyperoxide can be selected from a group comprising sodium hyperoxide, potassium hyperoxide, and lithium hyperoxide.

In a preferred and non-limiting embodiment, example, or aspect, the at least one alkali hyperoxide can be potassium hyperoxide.

In a preferred and non-limiting embodiment, example, or aspect, the earth alkali hyperoxide can be selected from a group comprising magnesium hyperoxide, calcium hyperoxide, strontium hyperoxide and barium hyperoxide.

In a preferred and non-limiting embodiment, example, or aspect, the alkali hyperoxide can be provided in the interior space of the cartridge.

In a preferred and non-limiting embodiment, example, or aspect, the alkali hyperoxide can be provided in the inner canister of the cartridge.

In a preferred and non-limiting embodiment, example, or aspect, the alkali hyperoxide can be a granular solid compound.

In a preferred and non-limiting embodiment, example, or aspect, when the alkali hyperoxide, such as, in a preferred and non-limiting embodiment, example, or aspect, potassium hyperoxide, is contacted with water, in a preferred and non-limiting embodiment, example, or aspect, water present in exhaled air, an alkaline solution can be formed that can act as an electrolyte. In a preferred and non-limiting embodiment, example, or aspect, the moisture (water) in exhaled air can be sufficient to provide an alkaline electrolyte solution.

In a preferred and non-limiting embodiment, example, or aspect, the alkali hyperoxide compound can be provided in the inner canister, in a preferred and non-limiting embodiment, example, or aspect, within the cartridge. The inner canister can have a porous, ion permeable canister wall, in a preferred and non-limiting embodiment, example, or aspect in the form of a permeable membrane or a porous metal wall.

In a preferred and non-limiting embodiment, example, or aspect, the cartridge can have at least one supporting structure provided inside the inner canister for supporting and storing the at least one alkali hyperoxide or earth alkali hyperoxide. In a preferred and non-limiting embodiment, example, or aspect, the supporting structure can avoid or prevent agglomeration of the alkali hyperoxide. The supporting structure can be a porous material, such as wire mesh, in a preferred and non-limiting embodiment, example, or aspect, a metal wire mesh, or a perforated plate (with a hole size of, in a preferred and non-limiting embodiment, example, or aspect, about 3 mm).

In a preferred and non-limiting embodiment, example, or aspect, where the porous material is a metal wire mesh, the metal wire mesh can also serve as the first metallic material as will be explained below in more detail.

In a preferred and non-limiting embodiment, example, or aspect, the supporting structure can divide an interior space of the inner canister into several sections or sub-spaces. In a preferred and non-limiting embodiment, example, or aspect, the sections can be of the same size or different sizes. In a preferred and non-limiting embodiment, example, or aspect, the sections can be arranged vertically (in the flow direction of the inhaled gas through the cartridge) or can be arranged in a grid or lattice form.

In a preferred and non-limiting embodiment, example, or aspect, in order to generate an electrical current or voltage, the at least one first metallic material and the at least one second metallic material can include different materials that can have different standard potentials.

In a preferred and non-limiting embodiment, example, or aspect, the at least one first metallic material and the at least one second metallic material can be selected such that the difference of the standard potential between both materials can provide a minimum voltage of at least 100 mV, preferably at least 200 mV, or more preferably at least 400 mV.

In a preferred and non-limiting embodiment, example, or aspect, the first metallic material provided in the interior space of the inner canister can be of a first metal or metal oxide that has a lower standard potential than the second metallic material or metal oxide.

In a preferred and non-limiting embodiment, example, or aspect, the first metallic material can have a higher standard potential than the second metallic material.

In a preferred and non-limiting embodiment, example, or aspect, any suitable combination of any suitable metal or metal oxide can be used as the first and second metallic materials as long as there is a sufficient difference in the standard potential of said first and second metallic materials.

In a preferred and non-limiting embodiment, example, or aspect, the first metallic material can be a first metal such as, in a preferred and non-limiting embodiment, example, or aspect, aluminum, zinc, manganese, or any combination thereof and the second metallic material can be a second metal, in a preferred and non-limiting embodiment, example, or aspect, iron, lead, copper, silver, hopcalite or any combination thereof; or vice versa.

In a preferred and non-limiting embodiment, example, or aspect, the first metallic material can be provided in the form of a metal wire mesh.

In a preferred and non-limiting embodiment, example, or aspect, the first metallic material can be provided in the form of a rod, or a plate, or any other suitable shape.

In a preferred and non-limiting embodiment, example, or aspect, the at least one first metallic material can be provided in the form of metallic particles dispersed in the alkali hyperoxide or earth alkali hyperoxide. In a preferred and non-limiting embodiment, example, or aspect, zinc particles can be dispersed in the alkali hyperoxide or earth alkali hyperoxide.

In a preferred and non-limiting embodiment, example, or aspect, the at least one first metallic material can be connected to at least one first electrode. In a preferred and non-limiting embodiment, example, or aspect, the first electrode can be made of any suitable conducting material such as metal, conducting polymer, etc. In a preferred and non-limiting embodiment, example, or aspect, the first metallic material can be dispersed in the form of particles in the alkali hyperoxide, whereupon the first electrode can be provided within the dispersion.

In a preferred and non-limiting embodiment, example, or aspect, the at least one second metallic material can be provided as a separate entity between the inner and outer canister.

In a preferred and non-limiting embodiment, example, or aspect, the providing of the at least one second metallic material as a separate entity between the inner and outer canister can be done in different ways. In a preferred and non-limiting embodiment, example, or aspect, the at least one second metallic material can be provided as a rod or plate in the space between the inner canister wall and the outer canister wall, in a preferred and non-limiting embodiment, example, or aspect, without contact to one of the canister walls.

In a preferred and non-limiting embodiment, example, or aspect, the second metallic material can be provided in the form of metallic particles that are placed between the inner and outer canisters. In a preferred and non-limiting embodiment, example, or aspect, the metallic particles can be arranged in an enclosed space between the ion-permeable membrane and the outer canister. In a preferred and non-limiting embodiment, example, or aspect, walls of the enclosed space can be made of a porous material. In a preferred and non-limiting embodiment, example, or aspect, the porous material can be in the form of a perforated plate. In a preferred and non-limiting embodiment, example, or aspect, the second metallic material can be dispersed as particles in a suitable carrier compound or in an additional $CO_2$ absorbing compound.

In a preferred and non-limiting embodiment, example, or aspect, the at least one second metallic material can be placed or fastened on the inner surface of the outer canister wall, such as, in a preferred and non-limiting embodiment, example, or aspect, directly on the inner surface or within a predefined distance of the inner surface of the outer canister wall. In a preferred and non-limiting embodiment, example, or aspect, the at least one second metallic material can be formed as a plate that is in contact with the outer canister wall.

In a preferred and non-limiting embodiment, example, or aspect, the at least one second metallic material can be at least partially integrated into the outer canister (wall). In a preferred and non-limiting embodiment, example, or aspect, the second metallic material can be integrated into the outer canister wall within a predefined portion or section of the wall. In a preferred and non-limiting embodiment, example, or aspect, the remaining part of the canister wall can be made of another material that does not conduct.

In a preferred and non-limiting embodiment, example, or aspect, the at least one second metallic material can be electrically connected to at least one second electrode. In a preferred and non-limiting embodiment, example, or aspect, the second electrode can be made of any suitable conducting material such as metal or a conductive polymer.

In a preferred and non-limiting embodiment, example, or aspect, the complete outer canister wall can serve as the second electrode. In a preferred and non-limiting embodiment, example, or aspect, the complete outer canister can be made of the second electrode material.

In a preferred and non-limiting embodiment, example, or aspect, in the cartridge, the ion permeable material arranged between inner and outer canister and separating the first and second electrode from each other can be a non-conducting material, such as, in a preferred and non-limiting embodiment, example, or aspect, a glass fleece, synthetic fleece or membrane. In a preferred and non-limiting embodiment, example, or aspect, the ion permeable material separating the first and second electrodes from each other can be permeable to liquid and can encompass, or cover partially or completely, the outer surface of the inner canister.

In a preferred and non-limiting embodiment, example, or aspect, in the cartridge, at least one $CO_2$ absorbing compound can be provided between the inner canister and the outer canister. In a preferred and non-limiting embodiment, example, or aspect, the $CO_2$ absorbing compound can be hopcalite (a mixture of manganese oxide and copper oxide), calcium hydroxide, sodium hydroxide, potassium hydroxide, barium hydroxide or mixtures thereof (also known as soda lime). In a preferred and non-limiting embodiment, example, or aspect, an alkali hyperoxide or earth alkali hyperoxide, such as potassium hyperoxide, can also be used as the $CO_2$ absorbing compound.

In a preferred and non-limiting embodiment, example, or aspect, the $CO_2$ absorbing compound can be arranged within the inner canister (in a preferred and non-limiting embodiment, example, or aspect, in the case of potassium hyperoxide) or can be arranged in the space between the inner and outer canister.

In a preferred and non-limiting embodiment, example, or aspect, the $CO_2$ absorbing compound can be arranged as a layer on the ion-permeable material (or ion-permeable membrane or layer) so that the $CO_2$ absorbing compound can be dispersed within the space between the inner and outer canister. In a preferred and non-limiting embodiment, example, or aspect, this can be done so that an enclosed space can be provided between the ion permeable layer and the outer canister wall that can be filled with the $CO_2$ absorbing compound or material. In a preferred and non-limiting embodiment, example, or aspect, the walls of the enclosed space can be made of a porous material, in a preferred and non-limiting embodiment, example, or aspect, in the form of a perforated plate. This can allow for a diffusion of $CO_2$ from the interior space of the inner canister through the ion-permeable wall thereof and the ion-permeable fleece through the perforated plate into the space filled with $CO_2$ absorbing compound.

In a preferred and non-limiting embodiment, example, or aspect, the $CO_2$ absorbing compound or material can be fixed on a mesh material or a fleece material that can be subsequently arranged on the ion-permeable fleece or material.

In a preferred and non-limiting embodiment, example, or aspect, the present cartridge can include at least one inlet for air, in a preferred and non-limiting embodiment, example, or aspect, exhaled air comprising $CO_2$ and water or moisture, and can include at least one outlet for oxygen generated in the cartridge. In a preferred and non-limiting embodiment, example, or aspect, the cartridge can be connected to a breathing hose and a breathing bag.

In a preferred and non-limiting embodiment, example, or aspect, the cartridge can be used in a breathing apparatus, in a preferred and non-limiting embodiment, example, or aspect, a CCBA.

In a preferred and non-limiting embodiment, example, or aspect, the present cartridge can enable the simultaneous generation of oxygen, and electrical energy, and the absorption of $CO_2$ when used. In a preferred and non-limiting embodiment, example, or aspect, air comprising $CO_2$ and water, in a preferred and non-limiting embodiment, example, or aspect, water contained in exhaled air, can enter the cartridge through the at least one inlet and can flow through the cartridge. In a preferred and non-limiting embodiment, example, or aspect, when the (moist) air contacts the at least one alkali hyperoxide or earth alkali hyperoxide provided in the cartridge, an (alkaline) electrolyte can be formed resulting in the generation of electrical energy and at the same time oxygen can be generated that leaves the cartridge through the at least one outlet.

According to a preferred and non-limiting embodiment, example, or aspect, provided is a cartridge for a breathing apparatus that can include a first perforated canister having an inner area; at least one of an alkali hyperoxide and an earth alkali hyperoxide provided in the inner area of the first perforated canister; a first metallic material provided in the inner area of the first perforated canister; a second metallic material provided proximate to an outside of the first perforated canister; and an ion permeable material provided between the first perforated canister and the second metallic material.

In a preferred and non-limiting embodiment, example, or aspect, the first perforated canister can include a porous wall.

In a preferred and non-limiting embodiment, example, or aspect, the second metallic material can be in the form of a second canister, and the first perforated canister can be provided in the second canister.

In a preferred and non-limiting embodiment, example, or aspect, the alkali hyperoxide can include at least one of the following: sodium hyperoxide, potassium hyperoxide, lithium hyperoxide, or any combination thereof.

In a preferred and non-limiting embodiment, example, or aspect, the earth alkali hyperoxide can include at least one of the following: magnesium hyperoxide, calcium hyperoxide, strontium hyperoxide, barium hyperoxide, or any combination thereof.

In a preferred and non-limiting embodiment, example, or aspect, the first and second metallic materials can differ from each other and can have different standard potentials.

In a preferred and non-limiting embodiment, example, or aspect, the standard potential between the first and second metallic materials can provide a minimum voltage of at least about 100 mV.

In a preferred and non-limiting embodiment, example, or aspect, the first metallic material can include at least one of the following: aluminum, zinc, manganese, or any combination thereof.

In a preferred and non-limiting embodiment, example, or aspect, the second metallic material can include at least one of the following: iron, lead, copper, silver, hopcalite, or any combination thereof.

In a preferred and non-limiting embodiment, example, or aspect, the first metallic material can be in the form of at least one of the following: a wire mesh, a rod, a plate, or any combination thereof.

In a preferred and non-limiting embodiment, example, or aspect, the first metallic material can be in the form of metallic particles dispersed in the alkali hyperoxide.

In a preferred and non-limiting embodiment, example, or aspect, the first perforated canister can be positioned substantially within a second canister, and the second metallic material can be provided between the first canister and the second canister.

In a preferred and non-limiting embodiment, example, or aspect, the first perforated canister can be positioned substantially within a second canister, and the second metallic material can be provided on an inner surface of the second canister.

In a preferred and non-limiting embodiment, example, or aspect, the first perforated canister can be positioned substantially within a second canister, and the second metallic material can be at least partially integrated into a wall of the second canister.

In a preferred and non-limiting embodiment, example, or aspect, the ion permeable material can be non-conducting.

According to a preferred and non-limiting embodiment, example, or aspect, provided is a method for generating oxygen and electrical energy. The method includes (a) providing the cartridge described above, wherein the cartridge includes an inlet and an outlet; and (b) causing gas that includes water and $CO_2$ to flow through the inlet of the cartridge and into contact with the at least one of the alkali hyperoxide and the earth alkali hyperoxide which at least partially absorbs the $CO_2$ forming an electrolyte and which releases oxygen, wherein the oxygen leaves the cartridge through the outlet, wherein the electrolyte provides electrical energy between first and second electrodes connected to the first and second metallic materials.

Further preferred and non-limiting embodiments, examples, or aspects are set forth in the following numbered clauses.

Clause 1: A chemical cartridge for an oxygen generating breathing apparatus comprising an outer canister and an inner canister with an interior space, wherein: at least one alkali hyperoxide or earth alkali hyperoxide that can act as an electrolyte in the presence of moisture and at least one first metallic material are provided in the interior space of the inner canister; and at least one second metallic material is provided between the inner canister and the outer canister; wherein between the inner canister with the first metallic material and the outer canister with the second metallic material an ion permeable material is arranged.

Clause 2: The cartridge of clause 1, wherein the alkali hyperoxide can be selected from a group comprising sodium hyperoxide, potassium hyperoxide and lithium hyperoxide, preferably potassium hyperoxide.

Clause 3: The cartridge of clause 1 or 2, wherein at least one supporting structure for the at least one alkali hyperoxide or earth alkali hyperoxide can be provided within the interior space of the inner canister.

Clause 4: The cartridge of any one of clauses 1-3, wherein the at least one supporting structure can be a wire mesh, in particular a metal wire mesh.

Clause 5: The cartridge of any one of clauses 1-4, wherein the first and second metallic materials differ from each other and have different standard potentials.

Clause 6: The cartridge of any one of clauses 1-5, wherein the first and second metallic material can be selected such that the difference of the standard potential between both metallic materials provides a minimum voltage of at least 100 mV, preferably at least 200 mV, in particular preferably at least 400 mV.

Clause 7: The cartridge of any one of clauses 1-6, wherein the at least one first metallic material can be provided in the form of a metal wire mesh, a rod or a plate.

Clause 8: The cartridge of any one of clauses 1-7, wherein the at least one first metallic material can be provided in the form of metallic particles dispersed in the alkali hyperoxide or earth alkali hyperoxide.

Clause 9: The cartridge of any one of clauses 1-8, wherein the at least one first metallic material can be connected to at least one first electrode.

Clause 10: The cartridge of any one of clauses 1-9, wherein the at least one second metallic material can be arranged in a space between the inner canister and the outer canister.

Clause 11: The cartridge of any one of clauses 1-10, wherein the at least one second metallic material can be arranged on the inner surface of the outer canister.

Clause 12: The cartridge of any one of clauses 1-11, wherein the at least one second metallic material can be integrated into the outer canister wall within a predefined portion or section of the outer canister wall.

Clause 13: The cartridge of any one of clauses 1-12, wherein the at least one second metallic material can be connected to at least one second electrode.

Clause 14: The cartridge of any one of clauses 1-13, wherein the complete outer canister functions as the at least one second electrode.

Clause 15: The cartridge of any one of clauses 1-14, wherein the ion permeable material arranged between inner and outer canister can be made of a non-conducting material.

Clause 16: The cartridge of any one of clauses 1-15, wherein at least one $CO_2$ absorbing compound can be provided.

Clause 17: The cartridge of any one of clauses 1-16, wherein at least one inlet for air and at least one outlet for oxygen generated in the cartridge.

Clause 18: A breathing apparatus comprising at least one cartridge according to any one of clauses 1-17.

Clause 19: A process for generating electrical energy and oxygen in a breathing apparatus according to clause 18: wherein air comprising $CO_2$ and moisture enters the cartridge through the at least one inlet and flows through the cartridge: wherein when the air contacts at least one alkali hyperoxide or earth alkali hyperoxide provided in the cartridge an electrolyte can be formed resulting in the generation of electrical energy and simultaneously oxygen; and wherein the generated oxygen leaves the cartridge through at least one outlet.

Clause 20: A cartridge for a breathing apparatus includes a first perforated canister having an inner area; at least one of an alkali hyperoxide and an earth alkali hyperoxide provided in the inner area of the first perforated canister; a first metallic material provided in the inner area of the first perforated canister; a second metallic material provided proximate to an outside of the first perforated canister; and an ion permeable material provided between the first perforated canister and the second metallic material.

Clause 21: The cartridge of clause 20, wherein the first perforated canister can include a porous wall.

Clause 22: The cartridge of clause 20 or 21, wherein the second metallic material can be in the form of a second canister and the first perforated canister can be provided in the second canister.

Clause 23: The cartridge of any one of clauses 20-22, wherein the alkali hyperoxide can include at least one of the following: sodium hyperoxide, potassium hyperoxide, lithium hyperoxide, or any combination thereof.

Clause 24: The cartridge of any one of clauses 20-23, wherein the earth alkali hyperoxide includes at least one of the following: magnesium hyperoxide, calcium hyperoxide, strontium hyperoxide, barium hyperoxide, or any combination thereof.

Clause 25: The cartridge of any one of clauses 20-24, wherein the first and second metallic materials differ from each other and have different standard potentials.

Clause 26: The cartridge of any one of clauses 20-25, wherein the standard potential between the first and second metallic materials provides a minimum voltage of at least about 100 mV.

Clause 27: The cartridge of any one of clauses 20-26, wherein the first metallic material includes at least one of the following: aluminum, zinc, manganese, or any combination thereof.

Clause 28: The cartridge of any one of clauses 20-27, wherein the second metallic material includes at least one of the following: iron, lead, copper, silver, hopcalite, or any combination thereof.

Clause 29: The cartridge of any one of clauses 20-28, wherein the first metallic material is in the form of at least one of the following: a wire mesh, a rod, a plate, or any combination thereof.

Clause 30: The cartridge of any one of clauses 20-29, wherein the first metallic material is in the form of metallic particles dispersed in the alkali hyperoxide.

Clause 31: The cartridge of any one of clauses 20-30, wherein the first perforated canister is positioned substantially within a second canister, and the second metallic material is provided between the first canister and the second canister.

Clause 32: The cartridge of any one of clauses 20-31, wherein the first perforated canister is positioned substantially within a second canister, and the second metallic material is provided on an inner surface of the second canister.

Clause 33: The cartridge of any one of clauses 20-32, wherein the first perforated canister is positioned substantially within a second canister, and the second metallic material is at least partially integrated into a wall of the second canister.

Clause 34: The cartridge of any one of clauses 20-33, wherein the ion permeable material is non-conducting.

Clause 35: A method for generating oxygen and electrical energy, the method comprising: (a) providing the cartridge of any one of clauses 20-34, wherein the cartridge includes an inlet and an outlet; and (b) causing gas that includes water and $CO_2$ to flow through the inlet of the cartridge and into contact with the at least one of the alkali hyperoxide and the earth alkali hyperoxide which at least partially absorbs the $CO_2$ forming an electrolyte and which releases oxygen, wherein the oxygen leaves the cartridge through the outlet, wherein the electrolyte provides electrical energy between first and second electrodes connected to the first and second metallic materials.

BRIEF DESCRIPTION OF THE DRAWINGS

Additional advantages and details of the invention are explained in greater detail below with reference to the exemplary preferred and non-limiting embodiments, examples, or aspects that are illustrated in the accompanying schematic figures, in which:

FIG. 1 is a cross-sectional view of an embodiment, example, or aspect of a cartridge for a breathing apparatus according to the principles of the present invention; and FIG. 2 is a cross-sectional view of another embodiment, example, or aspect of a cartridge for a breathing apparatus according to the principles of the present invention.

DESCRIPTION OF THE INVENTION

For the purposes of the following detailed description, it is to be understood that the invention may assume various alternative variations and step sequences, except where expressly specified to the contrary. It is also to be understood that the specific devices and methods described in the following specification are simply exemplary embodiments, examples, or aspects of the invention. Moreover, other than in any operating examples, or where otherwise indicated, all numbers expressing, in preferred and non-limiting embodiments, examples, or aspects, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the Doctrine of Equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

It is also to be understood that the specific devices and processes illustrated in the attached drawings, and described in the following specification, are simply exemplary embodiments, examples, or aspects of the invention. Hence, specific dimensions and other physical characteristics related to the embodiments, examples, or aspects disclosed herein are not to be considered as limiting. Certain preferred and non-limiting embodiments, examples, or aspects of the present invention will be described with reference to the accompanying figures where like reference numbers correspond to like or functionally equivalent elements.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise.

The present disclosure is directed to a cartridge for a breathing apparatus that can generate electrical energy. A first preferred and non-limiting embodiment, example, or aspect of the cartridge 10 shown in FIG. 1 includes an outer canister 11, an inner canister 12 and an ion permeable separator such as a glass fleece 14 arranged in a space between the outer canister 11 and inner canister 12. The walls of the inner canister 12 are made of a perforated material, such as a perforated metal plate allowing the diffusion of the gas therethrough.

In a preferred and non-limiting embodiment, example, or aspect, the interior space 13 of the inner canister 12 can be filled with potassium hyperoxide ($KO_2$) 15 that can be held in place within the inner canister 12 by means of, in a preferred and non-limiting embodiment, example, or aspect, a metal wire mesh 16 supporting structure. Depending on the dimension and construction of the mesh, the mesh 16 can create several sections for storing the alkali hyperoxide thereby preventing an agglomeration of the hyperoxide. In a preferred and non-limiting embodiment, example, or aspect, the wire mesh 16 can made of a first metal such as aluminum and is connected to a first electrode 17.

In a preferred and non-limiting embodiment, example, or aspect, the outer canister 11 can be made of a second metal such as iron or copper (with a higher standard potential than aluminum) and can serve as the second metal connected to a second electrode 18. The cartridge can form a part of a CCBA when used by a person, the exhaled air comprising $CO_2$ and water can enter the cartridge through the inlet 20 and flows into the inner canister 12. Here the moist air contacts the potassium hyperoxide 15 causing the formation of potassium hydroxide which acts as an alkaline electrolyte. Due to the electrolyte formation, a voltage between the first electrode and the second electrode is generated. At the same time oxygen is released from the potassium hyperoxide that leaves the cartridge through the outlet 30. $CO_2$ is absorbed by potassium hyperoxide 15.

FIG. 2 shows a second preferred and non-limiting embodiment, example, or aspect of the present cartridge. The preferred and non-limiting embodiment, example, or aspect of FIG. 2 differs from the preferred and non-limiting embodiment, example, or aspect of FIG. 1 in that no supporting structure is provided within the inner canister. Rather, zinc particles 21 are dispersed in the potassium hyperoxide 15 serving as first metal. Furthermore, a separate first electrode 17 is placed within the potassium hyperoxide and zinc particle dispersion.

Additionally, in a preferred and non-limiting embodiment, example, or aspect, a layer of hopcalite 19 serving as the second metal is provided between the ion-permeable separator 14 and the outer canister wall. For this reason an enclosed space is provided between the ion permeable separator 14 and the outer canister wall that is filled with the hopcalite 19. The walls of the enclosed space are made of a porous material, for instance in the form of a perforated plate. The hopcalite 19 serves as the second metal and is connected to a second electrode 18.

In a preferred and non-limiting embodiment, example, or aspect, the $CO_2$ of the exhaled air flows from the inner canister through the ion- and gas-permeable separator 14 and is subsequently absorbed by the $CO_2$ absorber 19.

In a preferred and non-limiting embodiment, example, or aspect, a canister 10 is arranged as an Alkaline-Manganese-Cell. The canister consists of a porous inner container, filled with a mixture of $KO_2$ 15 and zinc particles 21. The inner canister has a gas inlet and a gas outlet.

In a preferred and non-limiting embodiment, example, or aspect, within the $KO_2$-zinc mixture is located an electrode made of conductive material. The inner container is covered by a nonconductive membrane permeable to liquid and gas. The inner container with separator are covered by a layer of $MnO_2$ or Hopcalite. The Hopcalite layer is connected with a second electrode. The whole arrangement is covered by an outer canister.

In a preferred and non-limiting embodiment, example, or aspect, when the $KO_2$ canister will be used, exhaled air, enriched with $CO_2$ and moisture, will be applied to the $KO_2$. The reaction will start and oxygen will be generated. At the same time the $CO_2$ absorption will be started.

As can be seen, disclosed herein is a preferred and non-limiting embodiment, example, or aspect of cartridge 10 that includes outer canister 11, inner canister 12, and ion permeable separator 14 arranged in a space between outer canister 11 and inner canister 12. In a preferred and non-limiting embodiment, example, or aspect, ion permeable separator 14 can be glass fleece. However, this is not to be construed in a limiting sense since it is envisioned that ion permeable separator 14 can be formed of any suitable and/or desirable material that is permeable to ions for the application described herein. In an example, ion permeable separator 14 can be a synthetic fleece.

In a preferred and non-limiting embodiment, example, or aspect, the walls of inner canister 12 can be perforated or made of a perforated material. In a preferred and non-limiting embodiment, example, or aspect, the walls of inner canister 12 can be a perforated metal plate allowing the diffusion of a gas therethrough.

In a preferred and non-limiting embodiment, example, or aspect, an interior space 13 of inner canister 12 can, in a preferred and non-limiting embodiment, example, or aspect, be filled with alkali hyperoxide 15 that is held in place within inner canister 12 by any suitable and/or desirable means, such as, in a preferred and non-limiting embodiment, example, or aspect, a metal wire mesh 16 supporting structure. In a preferred and non-limiting embodiment, example, or aspect, alkali hyperoxide 15 can be the compound potassium hyperoxide ($KO_2$). However, this is not to be construed in a limiting sense since the use of any other suitable and/or desirable alkali hyperoxide compound is envisioned. For the purpose of description herein, alkali hyperoxide 15 will be described as being potassium hyperoxide. However, this is not to be construed in a limiting sense.

In a preferred and non-limiting embodiment, example, or aspect, depending on the dimension and construction thereof, mesh 16 can define several sections for storing alkali hyperoxide 15 thereby avoiding an agglomeration of the alkali hyperoxide 15.

In a preferred and non-limiting embodiment, example, or aspect, wire mesh 16 can be made of a first metal that can be connected to a first electrode 17. In a preferred and non-limiting embodiment, example, or aspect, the first metal can be aluminum. However, this is not to be construed in a limiting sense since it is envisioned that the first metal can be any other suitable and/or desirable metal or metal alloy.

In a preferred and non-limiting embodiment, example, or aspect, outer canister 11 can be made of a second metal. In a preferred and non-limiting embodiment, example, or aspect, the second metal can have a higher or greater standard potential than the first metal. In a preferred and non-limiting embodiment, example, or aspect the second metal can be iron or copper. The second metal can be connected to a second electrode 18. In a preferred and non-limiting embodiment, example, or aspect, it is envisioned that by appropriate selection of the first and second metals, the first metal can have a higher or greater standard potential than the second metal.

In a preferred and non-limiting embodiment, example, or aspect, cartridge 10 can form a part of a CCBA that when used by a person, exhaled air comprising $CO_2$ and water enters cartridge 10 through inlet 20 and flows into inner canister 12 via the perforations thereof. In inner canister 12 the moist air contacts the potassium hyperoxide 15 causing the formation of potassium hydroxide which acts as an alkaline electrolyte. Due to the alkaline electrolyte formation, a voltage between the first electrode 17 and the second electrode 18 is generated. At the same time, oxygen is released from the potassium hyperoxide 15 that leaves the cartridge through the outlet 30. $CO_2$ is absorbed by the potassium hyperoxide 15.

Also disclosed herein is a preferred and non-limiting embodiment, example, or aspect cartridge 10 that includes no supporting structure 16 within inner canister 12. In this preferred and non-limiting embodiment, example, or aspect, zinc particles 21 are dispersed in potassium hyperoxide 15 serving as the first metal. Furthermore, a separate first electrode 17 is placed within the potassium hyperoxide 15 and zinc particle 21 dispersion.

In a preferred and non-limiting embodiment, example, or aspect, a layer of hopcalite 19 serving as the second metal can be provided between the ion-permeable separator 14 and the wall of outer canister 11. For this reason an enclosed space (shown by the dashed line about hopcalite 19 in FIG. 2) can, in a preferred and non-limiting embodiment, example, or aspect, be provided between the ion permeable separator 14 and the wall of outer canister 11 that can be filled with the hopcalite 19. Walls of the enclosed space can be made of a porous material, in a preferred and non-limiting embodiment, example, or aspect, a perforated plate.

In a preferred and non-limiting embodiment, example, or aspect, hopcalite 19 can serve as the second metal and is connected to second electrode 18.

In a preferred and non-limiting embodiment, example, or aspect, $CO_2$ of the exhaled air entering inlet 20 flows into inner canister 12, through ion- and gas-permeable separator 14, and is subsequently absorbed by the hopcalite 19 acting as a $CO_2$ absorber.

Also disclosed herein is a preferred and non-limiting embodiment, example, or aspect cartridge 10 arranged as an Alkaline-Manganese-Cell. In this preferred and non-limiting embodiment, example, or aspect, cartridge 10 includes an outer container 11 and a porous inner container 12 filled with a mixture of $KOO_2$ 15 and zinc particles 21. Cartridge 10 has a gas inlet 20 and a gas outlet 30.

In a preferred and non-limiting embodiment, example, or aspect, within the $KO_2$-zinc mixture is located an electrode 17 made of conductive material. In a preferred and non-limiting embodiment, example, or aspect, the inner container 12 can be covered by a nonconductive membrane (or separator) 14 that is permeable to liquid and gas. In a preferred and non-limiting embodiment, example, or aspect, the inner container 12 and separator 14 can be covered by a layer of $MnO_2$ or hopcalite 19. In a preferred and non-limiting embodiment, example, or aspect, the layer of hopcalite 19 can be connected with a second electrode 18. The whole arrangement can be covered by an outer canister 11.

In a preferred and non-limiting embodiment, example, or aspect, when canister 10 is used, exhaled air, enriched with $CO_2$ and moisture, will be applied to the $KO_2$-zinc mixture. The reaction will start and oxygen will be generated. At the same time $CO_2$ absorption will be started.

In a preferred and non-limiting embodiment, example, or aspect, during the reaction, potassium hydroxide solution will be produced. The potassium hydroxide solution stays in contact both with the $KO_2$-zinc mixture (15, 21) and with the layer of hopcalite 19. Because of the different electrochemical potentials of zinc 21 (in the $KO_2$-zinc mixture) and manganese (in the hopcalite 19), an electrical voltage will be generated between electrodes 17 and 18. In a preferred and non-limiting embodiment, example, or aspect, this generated electrical voltage can be between 460 and 660 mV.

Also disclosed herein is a preferred and non-limiting embodiment, example, or aspect of a chemical cartridge for an oxygen generating breathing apparatus comprising an outer canister and an inner canister with an interior space, wherein: at least one alkali hyperoxide or earth alkali hyperoxide that can act as an electrolyte in the presence of moisture and at least one first metallic material are provided in the interior space of the inner canister; and at least one second metallic material is provided between the inner canister and the outer canister; wherein between the inner canister with the first metallic material and the outer canister with the second metallic material an ion permeable material is arranged.

In a preferred and non-limiting embodiment, example, or aspect, the alkali hyperoxide can be selected from a group comprising sodium hyperoxide, potassium hyperoxide, and lithium hyperoxide. In a preferred and non-limiting embodiment, example, or aspect, the alkali hyperoxide can desirably be potassium hyperoxide.

In a preferred and non-limiting embodiment, example, or aspect, at least one supporting structure for the at least one alkali hyperoxide or earth alkali hyperoxide can be provided within the interior space of the inner canister. The at least one supporting structure can be a wire mesh. In a preferred and non-limiting embodiment, example, or aspect, the wire mesh can be a metal wire mesh.

In a preferred and non-limiting embodiment, example, or aspect, the first and second metallic materials can differ from each other and can have different standard potentials.

In a preferred and non-limiting embodiment, example, or aspect, the first and second metallic material can be selected such that the difference of the standard potentials between both metallic materials can, in a preferred and non-limiting embodiment, example, or aspect, provide a minimum voltage of at least about 100 mV. In a preferred and non-limiting embodiment, example, or aspect, the difference of the standard potentials between both metallic materials can be at least about 200 mV. In a preferred and non-limiting embodiment, example, or aspect, the difference of the standard potentials between both metallic materials can be at least about 400 mV.

In a preferred and non-limiting embodiment, example, or aspect, the at least one first metallic material can be provided in the form of a metal wire mesh, a rod or a plate.

In a preferred and non-limiting embodiment, example, or aspect, the at least one first metallic material can be provided in the form of metallic particles dispersed in the alkali hyperoxide or earth alkali hyperoxide.

In a preferred and non-limiting embodiment, example, or aspect, the at least one first metallic material can be connected to at least one first electrode.

In a preferred and non-limiting embodiment, example, or aspect, the at least one second metallic material can be arranged in a space between the inner canister and the outer canister.

In a preferred and non-limiting embodiment, example, or aspect, the at least one second metallic material can be arranged on the inner surface of the outer canister.

In a preferred and non-limiting embodiment, example, or aspect, the at least one second metallic material can be integrated into the outer canister wall within a predefined portion or section of the outer canister wall.

In a preferred and non-limiting embodiment, example, or aspect, the at least one second metallic material can be connected to at least one second electrode.

In a preferred and non-limiting embodiment, example, or aspect, the complete outer canister can function as the at least one second electrode.

In a preferred and non-limiting embodiment, example, or aspect, the ion permeable material arranged between inner and outer canister can be made of a non-conducting material.

In a preferred and non-limiting embodiment, example, or aspect, at least one $CO_2$ absorbing compound can be provided.

In a preferred and non-limiting embodiment, example, or aspect, the cartridge can include at least one inlet for air and at least one outlet for oxygen generated in the cartridge.

Also disclosed herein is a breathing apparatus comprising at least one cartridge of the type described above.

Also disclosed herein is a process for generating electrical energy and oxygen in the breathing apparatus described above wherein air comprising $CO_2$ and moisture enters the cartridge through the at least one inlet and flows through the cartridge: wherein when the air contacts at least one alkali hyperoxide or earth alkali hyperoxide provided in the cartridge an electrolyte is formed resulting in the generation of electrical energy and simultaneously oxygen; and wherein the generated oxygen leaves the cartridge through at least one outlet.

Also disclosed herein is a cartridge (10) comprising: a first perforated canister (12) having an inner area; at least one of an alkali hyperoxide and an earth alkali hyperoxide (15) provided in the inner area of the first perforated canister (12); a first metallic material (16 or 21) provided in the inner area of the first perforated canister (12); a second metallic material (18 or 19) provided proximate to an outside of the first perforated canister (12); and an ion permeable material (14) provided between the first perforated canister (12) and the second metallic material.

In a preferred and non-limiting embodiment, example, or aspect, the first perforated canister (12) can include a porous wall.

In a preferred and non-limiting embodiment, example, or aspect, the second metallic material can be in the form of a second canister (11). The first perforated canister (12) can be provided in the second canister (11).

In a preferred and non-limiting embodiment, example, or aspect, the alkali hyperoxide can include at least one of the following: sodium hyperoxide, potassium hyperoxide, lithium hyperoxide, or any combination thereof. The earth alkali hyperoxide can include at least one of the following: magnesium hyperoxide, calcium hyperoxide, strontium hyperoxide, barium hyperoxide, or any combination thereof.

In a preferred and non-limiting embodiment, example, or aspect, the first and second metallic materials can differ from each other and can have different standard potentials.

In a preferred and non-limiting embodiment, example, or aspect, the standard potential between the first and second metallic materials can provide a minimum voltage of at least about 100 mV.

In a preferred and non-limiting embodiment, example, or aspect, the first metallic material can include at least one of the following: aluminum, zinc, manganese, or any combination thereof.

In a preferred and non-limiting embodiment, example, or aspect, the second metallic material can include at least one of the following: iron, lead, copper, silver, hopcalite, or any combination thereof.

In a preferred and non-limiting embodiment, example, or aspect, the first metallic material can be in the form of a wire mesh, a rod, a plate, or any combination thereof.

In a preferred and non-limiting embodiment, example, or aspect, the first metallic material can be in the form of metallic particles dispersed in the alkali hyperoxide.

In a preferred and non-limiting embodiment, example, or aspect, the first perforated canister (12) can be positioned substantially in a second canister (11). The second metallic material can be provided between the first canister and the second canister.

In a preferred and non-limiting embodiment, example, or aspect, the first perforated canister (12) can be positioned substantially in a second canister (11). The second metallic material can be provided on an inner surface of the second canister.

In a preferred and non-limiting embodiment, example, or aspect, the first perforated canister (12) can be positioned substantially in a second canister (11). The second metallic material can be at least partially integrated into a wall of the second canister.

In a preferred and non-limiting embodiment, example, or aspect, the ion permeable material can be non-conducting.

Also disclosed is a method for generating oxygen and electrical energy. The method includes: (a) providing the cartridge described above, wherein the cartridge includes an inlet and an outlet; and (b) causing gas that includes water and $CO_2$ to flow through the inlet of the cartridge and into contact with the at least one of the alkali hyperoxide and the earth alkali hyperoxide which at least partially absorbs the $CO_2$ forming an electrolyte and which releases oxygen, wherein the oxygen leaves the cartridge through the outlet, wherein the electrolyte provides electrical energy between first and second electrodes connected to the first and second metallic materials.

Although the invention has been described in detail for the purpose of illustration based on what is currently considered to be the most practical preferred and non-limiting embodiments, examples, or aspects, it is to be understood that such detail is solely for that purpose and that the invention is not limited to the disclosed preferred and non-limiting embodiments, examples, or aspects, but, on the contrary, is intended to cover modifications and equivalent arrangements that are within the spirit and scope of the appended claims. For example, it is to be understood that the present invention contemplates that, to the extent possible, one or more features of any preferred and non-limiting embodiment, example, or aspect can be combined with one or more features of any other preferred and non-limiting embodiment, example, or aspect.

The invention claimed is:
1. A cartridge for a breathing apparatus comprising:
a first perforated canister having an inner area;
at least one of an alkali hyperoxide and an earth alkali hyperoxide provided in the inner area of the first perforated canister;
a first metallic material provided in the inner area of the first perforated canister;
a second metallic material provided proximate to an outside of the first perforated canister; and
an ion permeable material provided between the first perforated canister and the second metallic material.

2. The cartridge of claim 1, wherein the first perforated canister includes a porous wall.

3. The cartridge of claim 1, wherein the second metallic material is in the form of a second canister, and the first perforated canister is provided in the second canister.

4. The cartridge of claim 1, wherein the alkali hyperoxide comprises at least one of the following: sodium hyperoxide, potassium hyperoxide, lithium hyperoxide, or any combination thereof.

5. The cartridge of claim 1, wherein the earth alkali hyperoxide comprises at least one of the following: magnesium hyperoxide, calcium hyperoxide, strontium hyperoxide, barium hyperoxide, or any combination thereof.

6. The cartridge of claim 1, wherein the first and second metallic materials differ from each other and have different standard potentials.

7. The cartridge of claim 6, wherein the standard potential between the first and second metallic materials provides a minimum voltage of at least about 100 mV.

8. The cartridge of claim 6, wherein the first metallic material comprises at least one of the following: aluminum, zinc, manganese, or any combination thereof.

9. The cartridge of claim 6, wherein the second metallic material comprises at least one of the following: iron, lead, copper, silver, hopcalite, or any combination thereof.

10. The cartridge of claim 1, wherein the first metallic material is in the form of at least one of the following: a wire mesh, a rod, a plate, or any combination thereof.

11. The cartridge of claim 1, wherein the first metallic material is in the form of metallic particles dispersed in the alkali hyperoxide.

12. The cartridge of claim 1, wherein the first perforated canister is positioned substantially within a second canister, and the second metallic material is provided between the first perforated canister and the second canister.

13. The cartridge of claim 12, wherein the first perforated canister is positioned substantially within a second canister, and the second metallic material is provided on an inner surface of the second canister.

14. The cartridge of claim 1, wherein the first perforated canister is positioned substantially within a second canister, and the second metallic material is at least partially integrated into a wall of the second canister.

15. The cartridge of claim 1, wherein the ion permeable material is non-conducting.

16. A method for generating oxygen and electrical energy, the method comprising:
(a) providing the cartridge of claim 1, wherein the cartridge includes an inlet and an outlet; and
(b) causing gas that includes water and $CO_2$ to flow through the inlet of the cartridge and into contact with the at least one of the alkali hyperoxide and the earth alkali hyperoxide which at least partially absorbs the $CO_2$ forming an electrolyte and which releases oxygen, wherein the oxygen leaves the cartridge through the outlet, wherein the electrolyte provides electrical energy between first and second electrodes connected to the first and second metallic materials.

* * * * *